United States Patent
Wilson et al.

(10) Patent No.: US 8,136,779 B2
(45) Date of Patent: Mar. 20, 2012

(54) MOUNTING ARRANGEMENT FOR A PRESSURIZED IRRIGATION SYSTEM

(75) Inventors: Daniel J. Wilson, Irvine, CA (US); James Y. Chon, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 12/844,257

(22) Filed: Jul. 27, 2010

(65) Prior Publication Data
US 2012/0025047 A1 Feb. 2, 2012

(51) Int. Cl.
*A47K 1/08* (2006.01)
(52) U.S. Cl. ............ 248/312; 222/105; 248/311.3
(58) Field of Classification Search ............ 248/312, 248/311.3, 312.1, 313, 314, 316.7; 604/31, 604/131, 153; 222/105, 148; 134/166 C
See application file for complete search history.

(56) References Cited

U.S. PATENT DOCUMENTS

| | | | |
|---|---|---|---|
| 3,589,363 A | 6/1971 | Banko et al. | |
| 4,029,094 A | 6/1977 | Winicki | |
| 4,184,510 A | 1/1980 | Brumbach | |
| 4,223,676 A | 9/1980 | Wuchinich et al. | |
| 4,246,902 A | 1/1981 | Martinez | |
| 4,411,652 A * | 10/1983 | Kramer et al. | 604/153 |
| 4,493,694 A | 1/1985 | Wuchinich | |
| 4,515,583 A | 5/1985 | Sorich | |
| 4,589,415 A | 5/1986 | Haaga | |
| 4,609,368 A | 9/1986 | Dotson, Jr. | |
| 4,813,927 A | 3/1989 | Morris et al. | |
| 4,869,715 A | 9/1989 | Sherburne | |
| 4,900,301 A | 2/1990 | Morris et al. | |
| 4,909,786 A | 3/1990 | Gijselhart et al. | |
| 4,922,902 A | 5/1990 | Wuchinich et al. | |
| 4,989,583 A | 2/1991 | Hood | |
| 5,032,111 A | 7/1991 | Morris et al. | |
| 5,047,009 A | 9/1991 | Morris et al. | |
| 5,154,694 A | 10/1992 | Kelman | |
| 5,160,317 A | 11/1992 | Costin | |
| 5,178,606 A | 1/1993 | Ognier et al. | |
| 5,179,606 A | 1/1993 | Kaihara et al. | |
| 5,279,547 A | 1/1994 | Costin | |
| 5,330,431 A | 7/1994 | Herskowitz | |
| 5,342,313 A | 8/1994 | Campbell et al. | |
| 5,359,996 A | 11/1994 | Hood | |
| 5,399,166 A | 3/1995 | Laing | |
| 5,403,276 A | 4/1995 | Schechter | |

(Continued)

FOREIGN PATENT DOCUMENTS

EP  1062958 A1  12/2000

(Continued)

OTHER PUBLICATIONS

International Searching Authority, International Search Report, PCT/US2011/042075, Sep. 7, 2011, 4 pages.

(Continued)

*Primary Examiner* — Ramon Ramirez

(57) ABSTRACT

An irrigation mounting arrangement for an irrigation container that is defined by a body portion, a neck member, and a stopper, is disclosed. The irrigation mounting arrangement comprises an upwardly extending base member and a mounting arm mechanism that extends away from the base member. The mounting arm mechanism includes at least one mounting aperture configured to selectively receive a portion of the irrigation container such that the neck member of the irrigation container is oriented above the body portion.

20 Claims, 12 Drawing Sheets

U.S. PATENT DOCUMENTS

| | | | |
|---|---|---|---|
| 5,520,633 A | | 5/1996 | Costin |
| 5,536,254 A | | 7/1996 | McVay |
| 5,586,973 A | | 12/1996 | Lemaire et al. |
| 5,591,127 A | | 1/1997 | Barwick, Jr. et al. |
| 5,643,304 A | | 7/1997 | Schechter et al. |
| 5,685,840 A | | 11/1997 | Schechter et al. |
| 5,697,525 A | * | 12/1997 | O'Reilly et al. ............. 222/105 |
| 5,700,240 A | | 12/1997 | Barwick, Jr. et al. |
| 5,733,256 A | | 3/1998 | Costin |
| 5,766,146 A | | 6/1998 | Barwick, Jr. et al. |
| 5,836,909 A | | 11/1998 | Cosmescu |
| 5,865,764 A | | 2/1999 | Moorehead |
| 6,083,189 A | | 7/2000 | Gonon et al. |
| 6,083,193 A | | 7/2000 | Kadziauskas |
| 6,126,129 A | * | 10/2000 | Herron ....................... 248/311.3 |
| 6,155,975 A | | 12/2000 | Urich et al. |
| 6,179,808 B1 | | 1/2001 | Boukhny et al. |
| 6,206,014 B1 | | 3/2001 | Cameron, III et al. |
| 6,450,215 B1 | | 9/2002 | Willemstyn et al. |
| 6,491,661 B1 | | 12/2002 | Boukhny et al. |
| 6,699,212 B1 | | 3/2004 | Kadziauskas et al. |
| 7,806,865 B1 | | 10/2010 | Wilson |
| 2002/0077587 A1 | | 6/2002 | Boukhny et al. |
| 2006/0100580 A1 | * | 5/2006 | Muller .......................... 604/152 |
| 2010/0012807 A1 | * | 1/2010 | Perman ......................... 248/312 |

FOREIGN PATENT DOCUMENTS

| | | |
|---|---|---|
| EP | 1062958 B1 | 4/2002 |
| FR | 2727847 A1 | 6/1996 |
| WO | WO 9008562 A1 | 8/1990 |
| WO | WO 9520373 A1 | 8/1995 |
| WO | WO 9520374 A1 | 8/1995 |
| WO | WO 9945868 A1 | 9/1999 |
| WO | WO 0027275 A1 | 5/2000 |
| WO | WO 0078372 A1 | 12/2000 |

OTHER PUBLICATIONS

International Searching Authority, Written Opinion of the International Searching Authority, PCT/ US2011/042075, Sep. 7, 2011, 3 pages.

* cited by examiner

MOUNTING ARRANGEMENT FOR A PRESSURIZED IRRIGATION SYSTEM

TECHNICAL FIELD

This disclosure relates generally to a pressurized irrigation system for surgical applications, and more specifically to a mounting arrangement for an irrigation supply.

BACKGROUND

In cataract surgery, it is important to control intraocular infusion pressure. Irrigation solution is commonly used to maintain both the anatomic and physiologic integrity of intraocular tissues during surgery. In known irrigation systems, irrigation fluid is supplied in a bag or bottle that is suspended on a pole in a "neck-down" position, with a supply tube extending from the lowermost portion of the irrigation supply source. In the "neck-down" position, air remains at the top of the bag or bottle.

In some systems, gravity feed methods 10 or pressurized gas sources 20 are used for controlling surgical irrigation pressure and flow of the irrigation system. Gravity feed irrigations methods 10, such as those illustrated in FIG. 1; provide a pressure and flow based on the height of the supply source 12. The higher the supply source above the eye, the greater the pressure and flow. The lower the supply source, the lower the pressure and flow. The surgeon controls the supply source height by raising or lowering the pole to which the supply source is mounted. Gravity feed methods have limitations on pressure response rates due to the requirements of raising and lowering the irrigation bottle.

Pressurized gas sources 20, such as those illustrated in FIG. 2, control the irrigation pressure by increasing or decreasing the pressure inside an irrigation bottle 23. The bottle 23 is suspended at a constant height and a gas pressure pump is connected to the bottle 23 (e.g., through line 32). While pressurized gas methods improve on the pressure response rates from the gravity feed method, pressurized gas methods require cumbersome venting snorkel devices that complicate the surgical setup. Further, both methods require filtering of air or gas into the bottle to prevent contamination which adds cost and complexity.

Other pressurized irrigation systems have used compression, combined with gravity, to deliver irrigation fluid to the surgical site. In such systems, a compliant irrigation bag is squeezed, thereby pushing the irrigation fluid into the system. However, in such systems, the squeezing action causes the bag volume and the geometry to change, which can change the neck position during use. Such changes can cause problems with the neck, associated tubing, and the pressurized system as a whole, because the neck may become trapped or pinched within the squeezing system.

Moreover, because prior art systems have the irrigation supply container oriented in a "neck-down" position, air is trapped at the top of the irrigation container. Thus, prior to use in surgery, the fluid management components, including the irrigation container, need to be purged of air or primed. While the priming and diagnostic system procedure is effective, it is unable to remove all of the air from within the irrigation supply container. This residual entrained air has a deleterious effect on overall system performance. For example, air trapped in the irrigation supply container can slow down the fast hydraulic response necessary for optimum performance.

Accordingly, there exists a need for an improved mounting arrangement for a pressurized irrigation supply that improves operation by reducing potential problems that occur during operation of an infusion system.

BRIEF SUMMARY

An irrigation mounting arrangement for an irrigation container that is defined by a body portion, a neck member, and a stopper, is disclosed. The irrigation mounting arrangement comprises an upwardly extending base member and a mounting arm mechanism that extends away from the base member. The mounting arm mechanism includes at least one mounting aperture configured to selectively receive a portion of the irrigation container such that the neck member of the irrigation container is oriented above the body portion.

BRIEF DESCRIPTION OF THE DRAWINGS

Embodiments of the present disclosure will now by described by way of example in greater detail with reference to the attached figures, in which.

DETAILED DESCRIPTION

Figure 1:
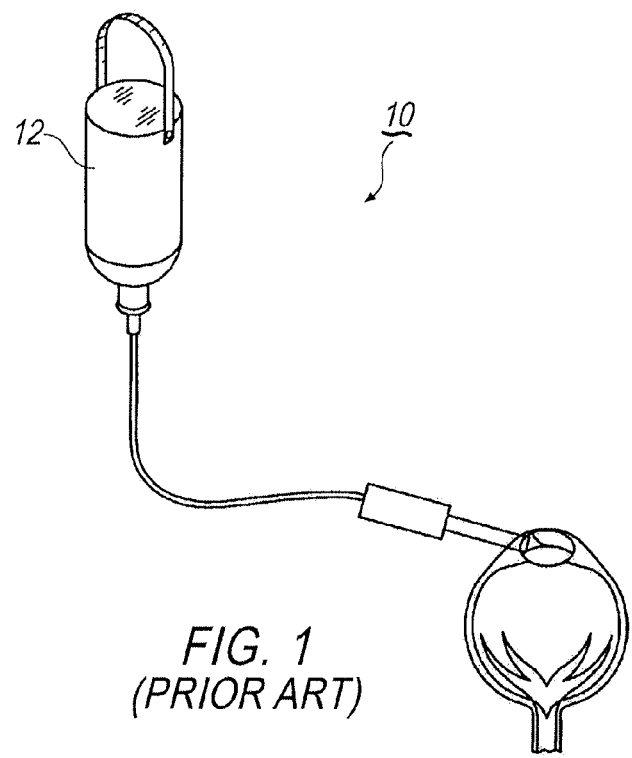
FIG. 1 is a prior art mounting arrangement for an irrigation fluid container.
Figure 2:
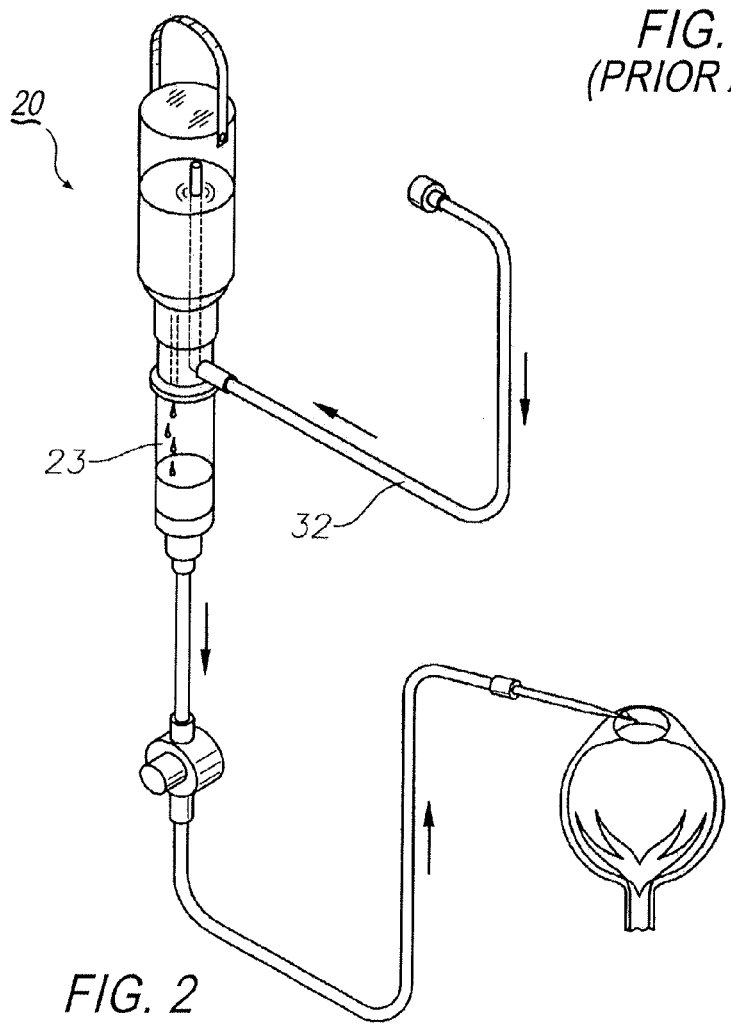
FIG. 2 is another prior art mounting arrangement of an irrigation fluid container.

Referring now to the discussion that follows and also to the drawings, illustrative approaches to the disclosed devices and methods are shown in detail. Although the drawings represent some possible approaches, the drawings are not necessarily to scale and certain features may be exaggerated, removed, or partially sectioned to better illustrate and explain the present disclosure. Further the descriptions set forth herein are not intended to be exhaustive or otherwise limit or restrict the claims to the precise forms and configurations shown in the drawings and disclosed in the following detailed descriptions.

Figure 3:
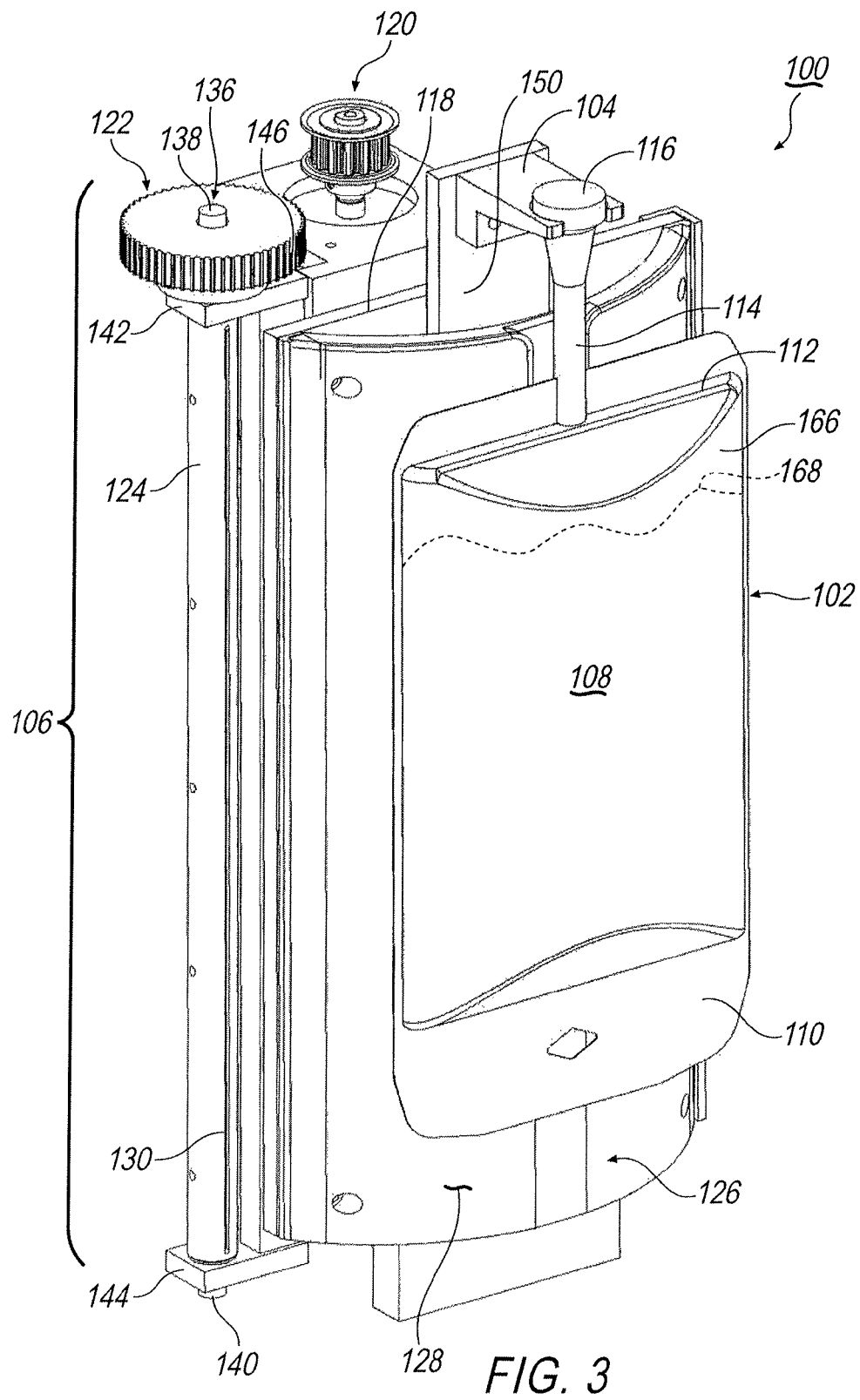
FIG. 3 is a first exemplary arrangement for an irrigation mounting system.
Figure 4:
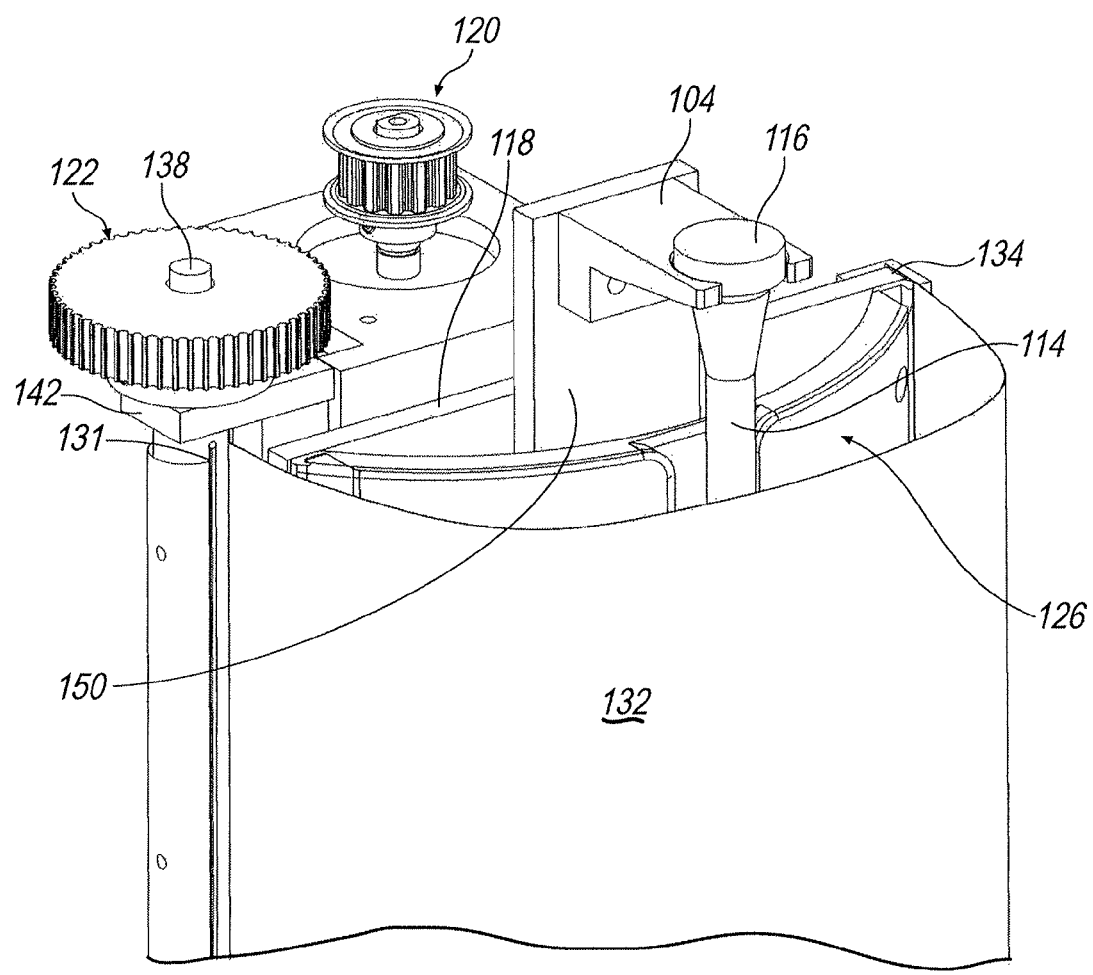
FIG. 4 an enlarged view of a top portion of the irrigation mounting system shown in FIG. 3.
Figure 5:
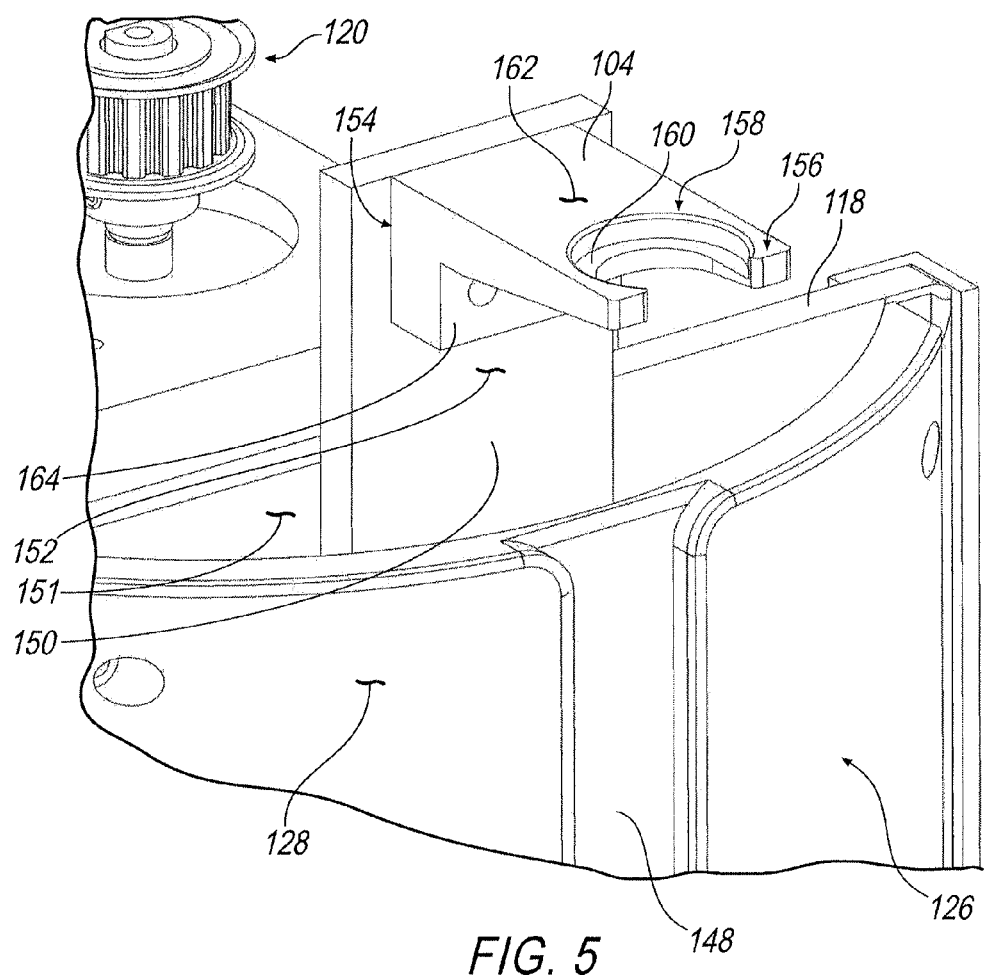
FIG. 5 is an enlarged view of the top portion of the irrigation mounting system shown in FIG. 3 with an irrigation container removed.

Referring to FIGS. 3-5 a first exemplary arrangement of an irrigation mounting system 100 is shown. Irrigation mounting system 100 comprises an irrigation container 102, a mounting arm 104, and an actuation device 106. Irrigation container 102 is configured as a compliant member, such as a compliant bag commonly supplied by Charter Medical, Lakewood, N.J., for surgical site infusion. Alternatively, irrigation container 102 may be configured as a custom container specifically designed for this application. Irrigation container 102 includes a body member 108, a first sealed end 110, and a second end 112 opposing first sealed end 110. Body member 108 may be made from any suitable material that provides container collapse without excessive stretching. A neck member 114 ends outwardly from second end 112 and includes a stopper member 116. Stopper member 116 effectively seals the neck member 114 such that fluid stored in irrigation container 102 is prevented from unintentionally exiting irrigation container 102. However, as is conventional, stopper member 116 may be selectively pierced with a stopper spike to fluidly connect irrigation container to a surgical handpiece.

Actuation device 106 includes a base member 118, a motor gear mount 120, an actuation gear 122, and a take-up reel 124. In one embodiment, secured to base member 118 is a platen 126. In one exemplary arrangement, platen 126 has a curved-shape configuration and is fixedly secured to base member 118 so as to form a convex mounting face 128.

Take-up reel 124 includes a slot member 130 into which a first edge 131 of a compressing band 132 is fixedly received. While compressing band 132 was removed from FIG. 3, it may be seen in FIG. 4. A second edge 134 of compressing band 132 is fixedly secured to either the platen or a portion of base member 118, opposite from take-up reel 124.

Take-up reel 124 includes a rod member 136 disposed within take-up reel 124. Rod member 136 is defined by a first end 138 and a second end 140. A portion of rod member 136 is fixedly attached to take-up reel 124. A first mounting flange 142 is positioned adjacent first end 138 of rod member 136. A second mounting flange 144 is positioned adjacent to second end 140 of rod member 136. Rod member 136 is mounted to first and second mounting flanges 142, 144 such that rod member 136 may be selectively rotated with respect to first and second mounting flanges 142, 144. First end 138 of rod member 136 is mounted to first mounting flange 142 such that it extends outwardly from a top surface 146 of first mounting flange 142. Actuation gear 122 is fixedly attached to first end 138 of rod member 136.

Motor gear mount 120 is operatively connected to a motor. A motor gear operatively connects to motor gear mount 120 and interconnects with actuation gear 122. In operation, as will be explained in more detail below, as the motor is activated, power is transmitted to actuation gear 122 causing actuation gear 122 to rotate. As actuation gear 122 rotates, take-up reel 124 rotates. Because first edge 131 of compressing band 132 is fixed to take-up reel 124, as take-up reel 124 is rotated in a first direction, compressing band 132 is wound up onto take-up reel 124. This action forces compressing band 132 to move towards platen 126, thereby compressing body member 108 of irrigation container 102 against platen 126. Take-up reel 124 may also be rotated in a second direction to unwind compressing band 132 from take-up reel 124, thereby providing clearance between platen 126 and compressing band 132 such that irrigation container 102 may be replaced.

A groove 148 is formed within platen 126. Groove 148 is configured to have a depth that is at least equal to the diameter of neck member 114. When irrigation container 102 is mounted to mounting arm 104, neck member 114 is disposed within groove 148 such that when compressing band 132 is actuated, neck member 114 does not become compressed or pinched between platen 126 and compressing band 132.

In one embodiment, mounting arm 104 is fixedly attached to a post member 150. Post member 150 is fixedly attached to base member 118 by any suitable manner so as to extend upwardly from a top edge of base member 118. For example, in the exemplary arrangement shown in FIG. 5, post member 150 is secured to a first face 151 of base member 118. In an alternative arrangement, post member 150 may have an end portion fixed to a top edge of base member 118 rather than to first face 151 of base member 118. In either embodiment, mounting arm 104 is arranged on post member 150 so as to extend outwardly from a mounting face 152 of post member 150. In yet another alternative embodiment, mounting arm 104 may be directly attached to base member 118.

As best seen in FIG. 5, mounting arm 104 comprises a mounting end 154 and a supporting end 156. When mounting arm 104 is secured to post member 150, supporting end 156 is disposed so as to be spaced away from mounting face 152 such that supporting end 156 is arranged over groove 148. The supporting end 156 is configured with a cut-out portion 158 and a supporting flange 160 formed therein. In one exemplary embodiment, supporting flange 160 is recessed below a top surface 162 of mounting arm 104, to be explained below in further detail.

Mounting end 154 may include an optional downwardly extending mounting flange 164 that abuts against mounting face 152 of post member 150. Thus, in one exemplary configuration, mounting flange 164 is generally configured as having an L-shaped cross-section. Suitable securing members are received within mounting flange 164 to secure supporting end 156 to post member 150. Alternatively, mounting arm 104 may be configured without mounting flange 164.

Referring to back to FIGS. 3 and 4, irrigation container 102 is secured to irrigation mounting system 100 such that stopper 116 is positioned within supporting end 156 of mounting arm 104. Supporting flange 160 serves to support stopper 116. In accordance with one aspect of the arrangement of irrigation mounting system 100, irrigation container 102 is oriented such that neck member 114 extends upwardly from body member 108. In other words, in contrast to the prior art, irrigation container 102 is oriented in a "neck-up" configuration. In this manner, air 166 within irrigation container 102 is disposed above the irrigation fluid 168 retained within irrigation container 102 such that it is in direct communication with neck member 114. Thus, when the system is primed for use, air may be effectively evacuated from irrigation container 102.

Figure 10:
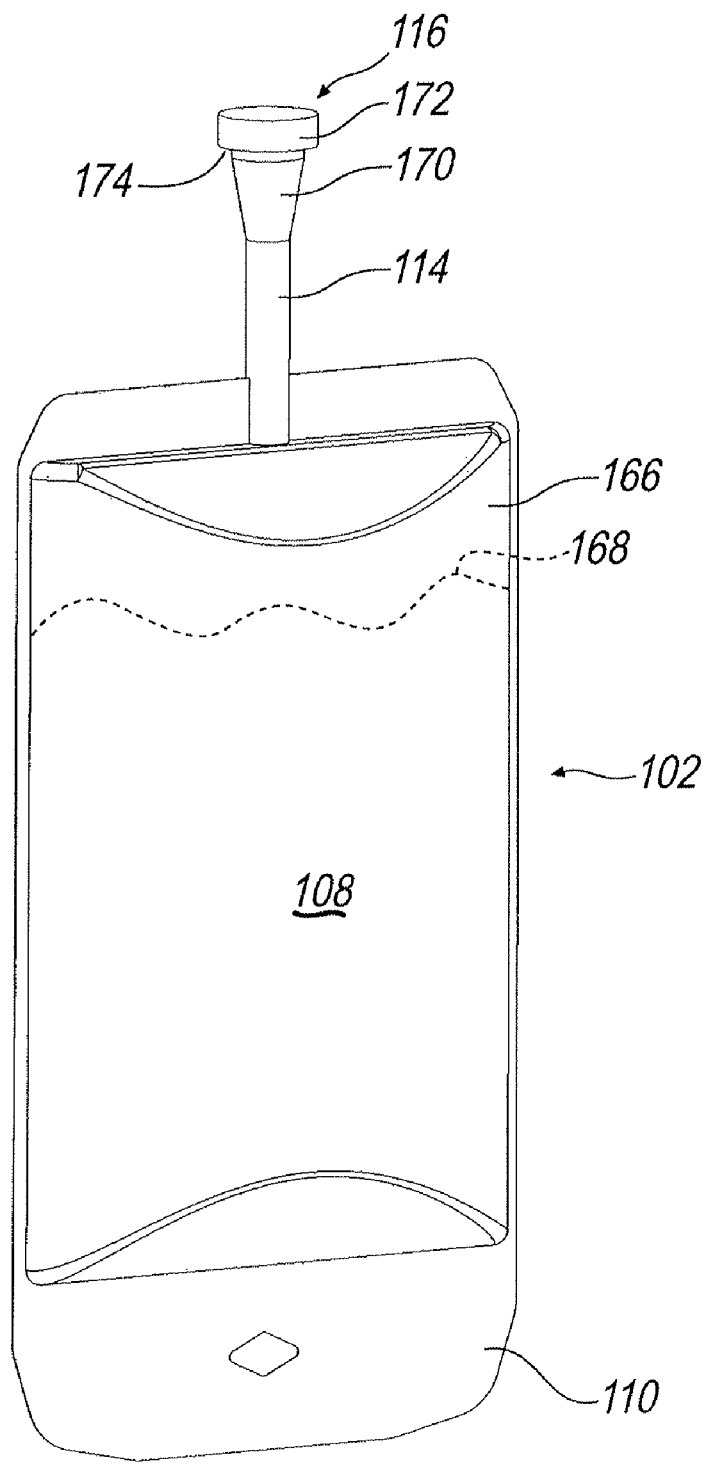
FIG. 10 is an elevational view of an irrigation container for use in an irrigation mounting system.

Referring to FIG. 10, in accordance with another aspect of the arrangement of irrigation mounting system 100, stopper member 116 may be configured with a frusto-conical shaped section 170 and a disc shaped distal end 172. The disc shaped distal end 172 is sized to fit within cut-out portion 158. A bottom surface 174 of disc shaped distal end 172 rests on supporting flange 160. In one exemplary configuration, stopper member 116 is positioned within cut-out portion 158 so as to form an articulating or gimbaled mount. In this manner, irrigation container 102 is positively and properly registered within irrigation mounting system 100 while permitting irrigation container 102 to change angles as irrigation container 102 is squeezed or depleted. Because stopper member 116 forms an articulating mount, the proper position of neck member 114 within groove 148 may be maintained during operation of compressing band 132, thereby preventing neck member 114 from getting inadvertently pinched or squeezed by compressing band 132.

In another exemplary arrangement, stopper 116 may be selectively fixedly engaged within cut-out 158. More specifically, stopper 116 may be sized so as to snap into cut-out 158 to positively and rigidly engage stopper 116 with mounting arm 104. This configuration provides a positive mount to permit spiking of stopper 116 to fluidly connect stopper 116 to the irrigation system. In the prior art, spiking of the stopper is typically accomplished by holding the irrigation container in one hand with the stopper facing the operator. However the irrigation container may slip, leading to inadvertent puncturing of the container or even the operator. Thus, a fixed engagement provides a support mechanism that prevents inadvertent movement of stopper 116 during the spiking operation.

Figure 11:
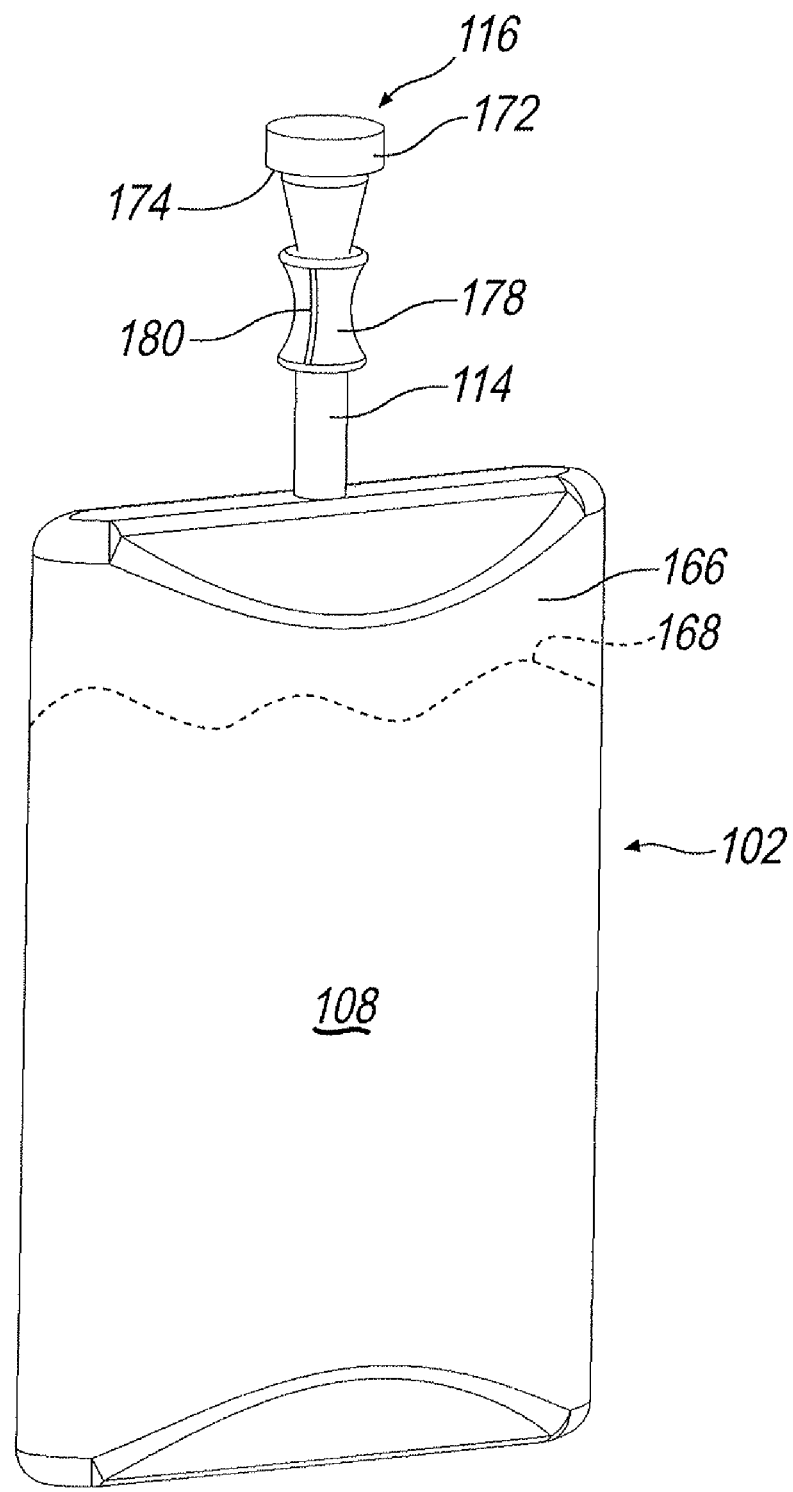
FIG. 11 is an elevational view of an alternative arrangement of an irrigation container for use in an irrigation mounting system.
Figure 12:
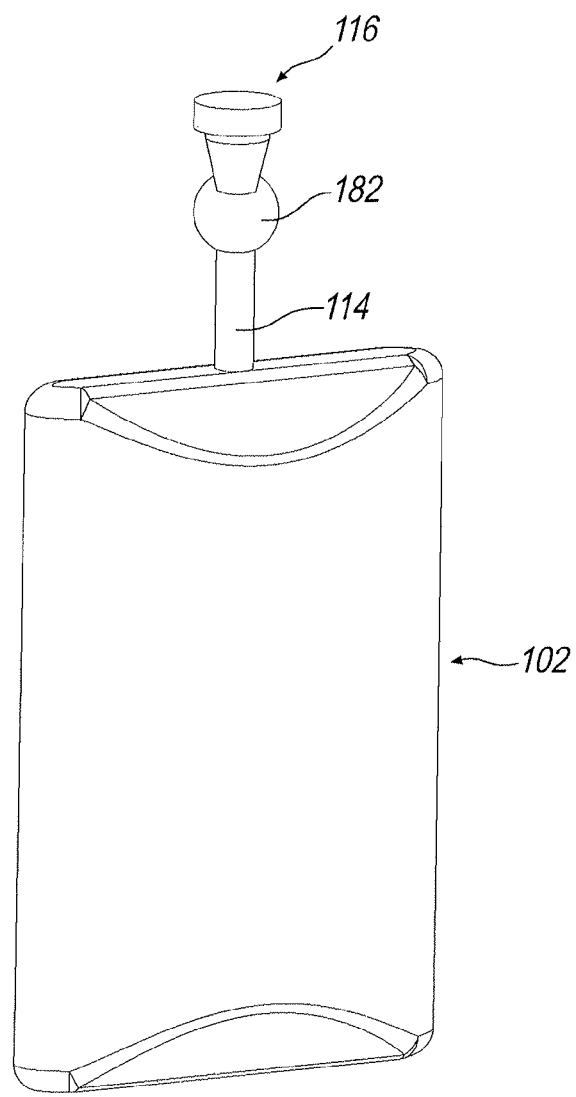
FIG. 12 is an elevational view of another alternative arrangement of an irrigation container for use in an irrigation mounting system.
Figure 13A:
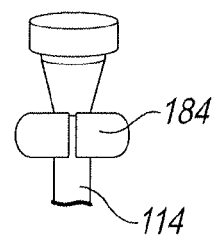
FIG. 13A is an embodiment of a clip member for use with an irrigation mounting system.
Figure 13B:
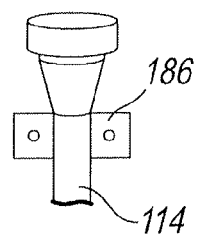
FIG. 13B is an alternative embodiment of a clip member for use with an irrigation mounting system.

Once stopper 116 has been spiked and fluidly connected to the irrigation system, stopper 116 may be selectively removed from mounting arm 104 and re-positioned on mounting arm 104 in an articulating mount. In one exemplary arrangement, a contoured clip member 178, best seen in FIG. 11, may be positioned on neck member 114, sufficiently below disc member 172 so as to permit disc member 172 to fixedly engage within cut-out 158 during the spiking operation. The contoured clip member 178 is formed such that clip member may engage with cut-out 158 to properly position irrigation container 102 within irrigation supply mounting system 100 and maintain irrigation container 102 in a "neck-up" position, while permitting articulation of irrigation supply container 102 as fluid is depleted. In one exemplary configuration, contoured clip member 178 may have an hourglass shape, such as that shown in FIG. 11. In the configuration shown in FIG. 11, clip member 178 may be constructed of a generally flexible material and include a slit 180 to permit clip member 178 to be easily secured to a standard neck member 114. While clip member 178 is shown as having an hourglass shape, it is understood that any suitable shape that would permit articulation of irrigation container 102 is contemplated by the present disclosure. For example, a ball shaped clip member 182 may be utilized, as shown in FIG. 12. A rod member 184 (FIG. 13A) that is orientated generally perpendicular to neck member 114 would also be suitable, as would a generally square member 186 (FIG. 13B) that receives mounting rods therethrough.

Figure 6:
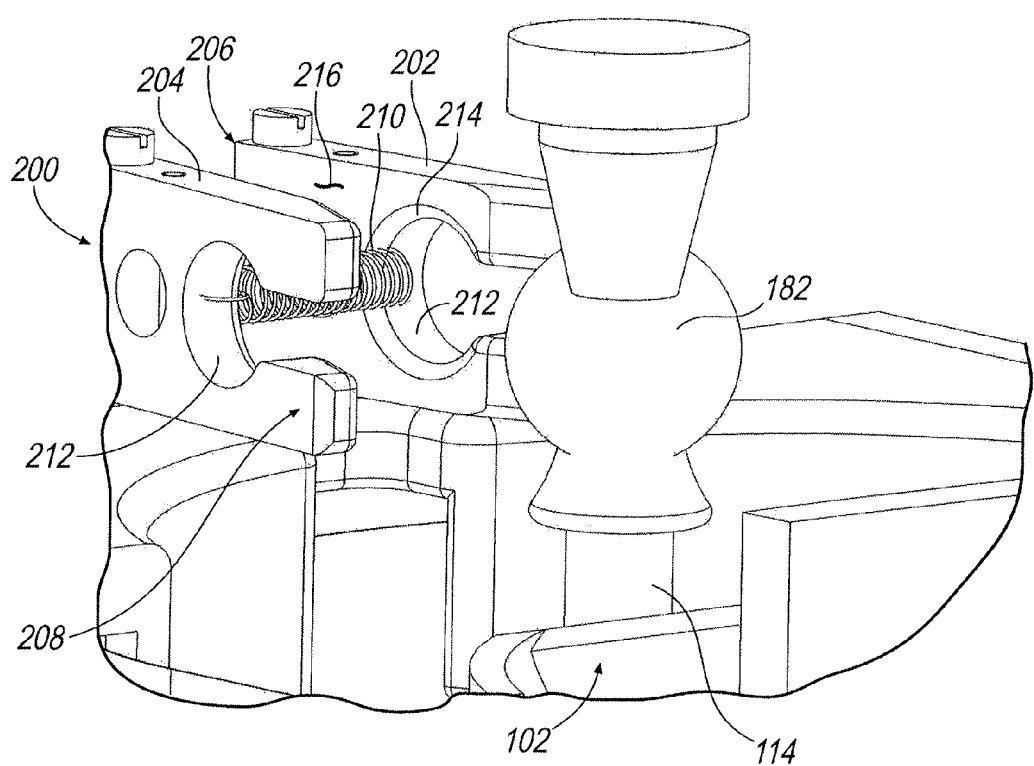
FIG. 6 is an enlarged view of a top portion of an alternative arrangement of an irrigation mounting system.

An alternative embodiment of a mounting arm mechanism 200 is shown in FIG. 6. In this configuration, mounting arm mechanism 200 includes laterally opposing first and second mounting arms 202, 204, each defined by a supporting end 206 and a mounting end 208. Supporting end 206 is pivotally connected to a base member (not seen) of an irrigation supply mounting assembly, such as that shown in FIG. 3. A biasing member 210 operatively connects first and second mounting arms 202, 204 together, a predetermined distance from one another. Formed within each mounting arm 202, 204 at mounting end 208 are mounting apertures 212. A supporting groove 214 may also be formed on an inner face 216 of each mounting arm 202, 204, adjacent mounting apertures 212.

As stated above, supporting end 206 of mounting arms 202, 204 are secured to a base member of an irrigation supply mounting assembly. Mounting arms 202, 204 are secured such that inner faces 216 of each mounting arms 202, 204 may pivot with respect to one another. Biasing member 217, which may be constructed as a helical spring or other suitable member, serves to keep mounting arms 202, 204 a predetermined distance from one another. However, application of a predetermined amount of force at mounting ends 208 on mounting arms 202, 204 may be applied to temporarily move mounting arms 202, 204 apart from one another to permit a mounting clip, such as mounting clip 182, to be received within mounting apertures 212. Once mounting clip 182 is positioned within mounting apertures 212, the predetermined force holding mounting arms 202, 204 apart is removed and biasing member 217 serves to return mounting arms 202, 204 to their predetermined positions while trapping clip member 182 within mounting apertures 212. In this manner, clip member 182 is positively retained within mounting arm mechanism 200 such that irrigation container 102 is oriented in a neck-up position. Accordingly, air entrained within irrigation container 102 may be effectively evacuated as part of the initial priming operation. Moreover, due to the configuration of mounting apertures 212, clip member 182 is configured to retain irrigation container 102 in an articulating manner such that as irrigation container 102 is squeezed or compressed and fluid is depleted therefrom, the angle of irrigation container 102 within the irrigation mounting system may selectively change without inadvertent pinching or compressing of neck member 114.

Figure 7:
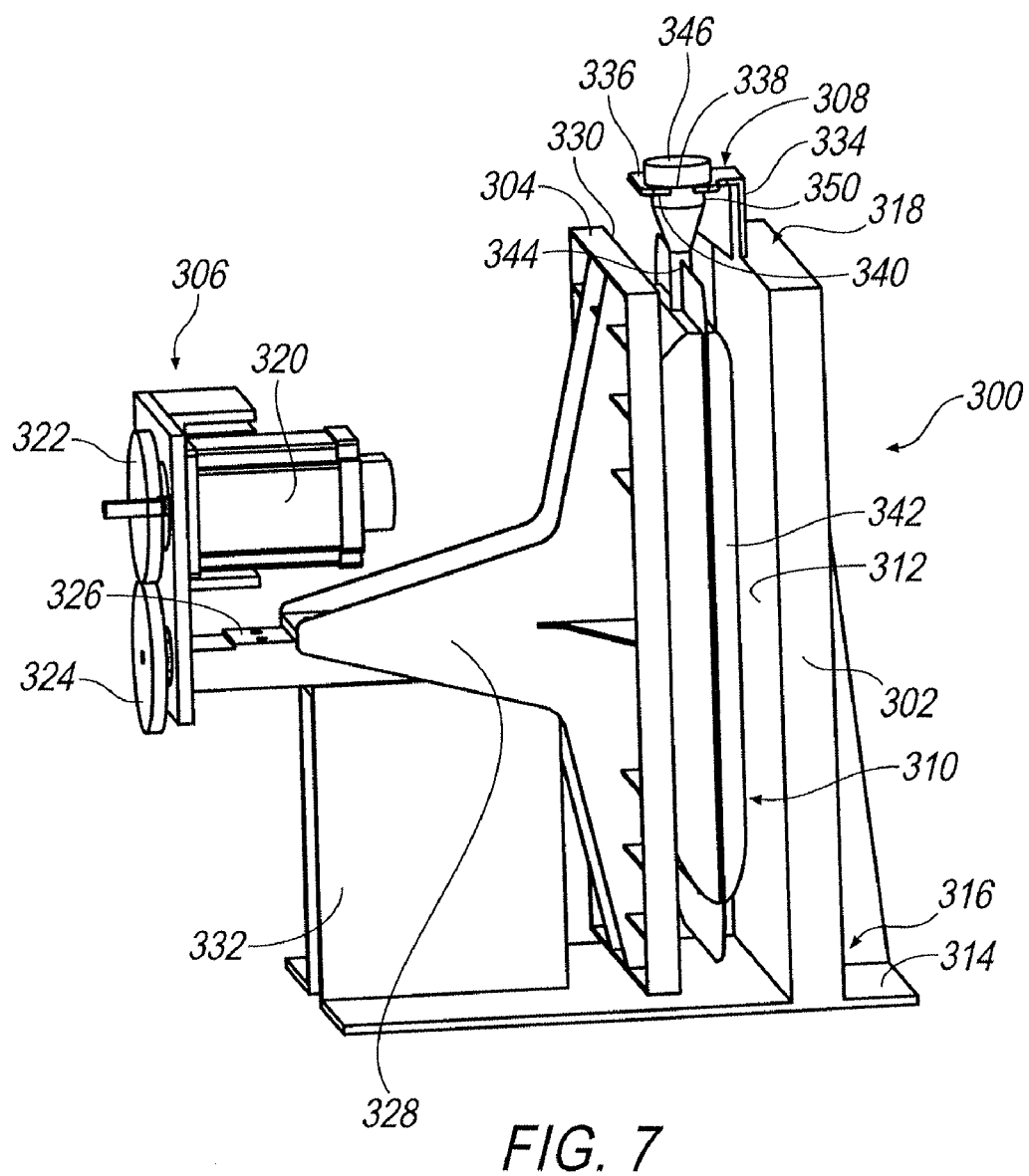
FIG. 7 is a perspective view of yet another alternative arrangement of an irrigation mounting system.
Figure 8:
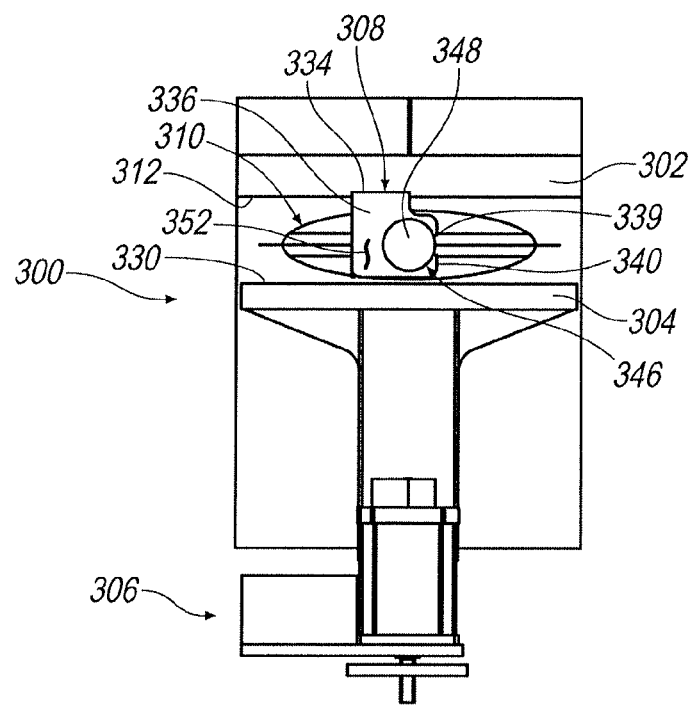
FIG. 8 is a top view of the irrigation mounting system arrangement of FIG. 7.
Figure 9:
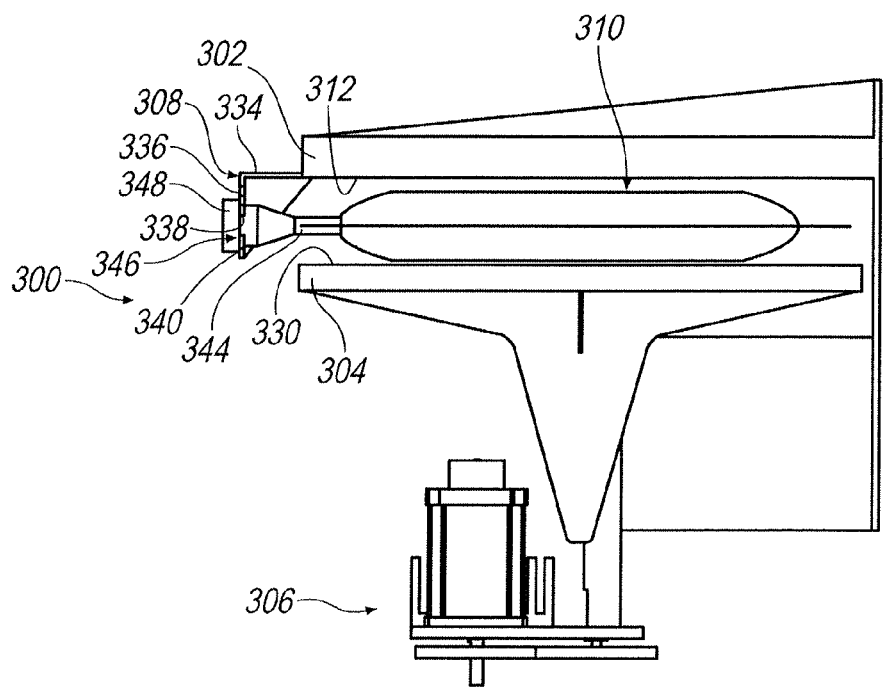
FIG. 9 is a sideways elevational view of the irrigation mounting system arrangement of FIG. 7.

Referring to FIGS. 7-9, an alternative embodiment of an irrigation mounting system 300 is depicted. Irrigation mounting system 300 comprises a generally planar first plate 302, a generally planar second plate 304, an actuation device 306, a mounting arm 308, and an irrigation container 310. The first plate 302 includes a front face 312. First plate 302 is configured so as to be mounted in a stationary manner. In one exemplary arrangement, irrigation mounting system 300 further comprises a mounting platform 314 to which a first end 316 of first plate 302 is fixed. Mounting arm 308 is secured to a second end 318 of first plate 302, to be explained in further detail below.

Actuation device 306 comprises a motor 320 that drives a motor gear 322. Motor gear 322 operatively engages a driving gear 324 that is fixed to a drive member 326. Drive member 326 is operatively engaged with an actuation arm 328 that is fixedly secured to second plate 304. As motor 320 is actuated in a first direction, motor gear 322 rotates driving gear 324 such that actuation aim 328 is moved laterally toward first plate 302 by drive member 326. Because second plate 304 is fixedly connected to actuation arm 328, as motor 320 is actuation in the first direction, a front face 330 of second plate 304 is moved laterally toward front face 312 of first plate 302. A support post 332 may be provided to serve as a guide and support for actuation arm 328. Support post 332 may be fixed to mounting platform 314.

As described above, secured to second end 318 of first plate 302 is mounting arm 308. Mounting arm includes an upwardly extending support member 334 and a generally laterally extending mounting platform 336. Mounting platform 336 is configured to extend laterally outwardly from front face 312 of first plate 302. Mounting platform 336 includes a mounting aperture 338 that has an opening 339 formed on a first side edge 340 thereof. Opening 339 is positioned so as to be facing away from first faces 312, 330 of first and second plates 302, 304, respectively.

Figure 14A:
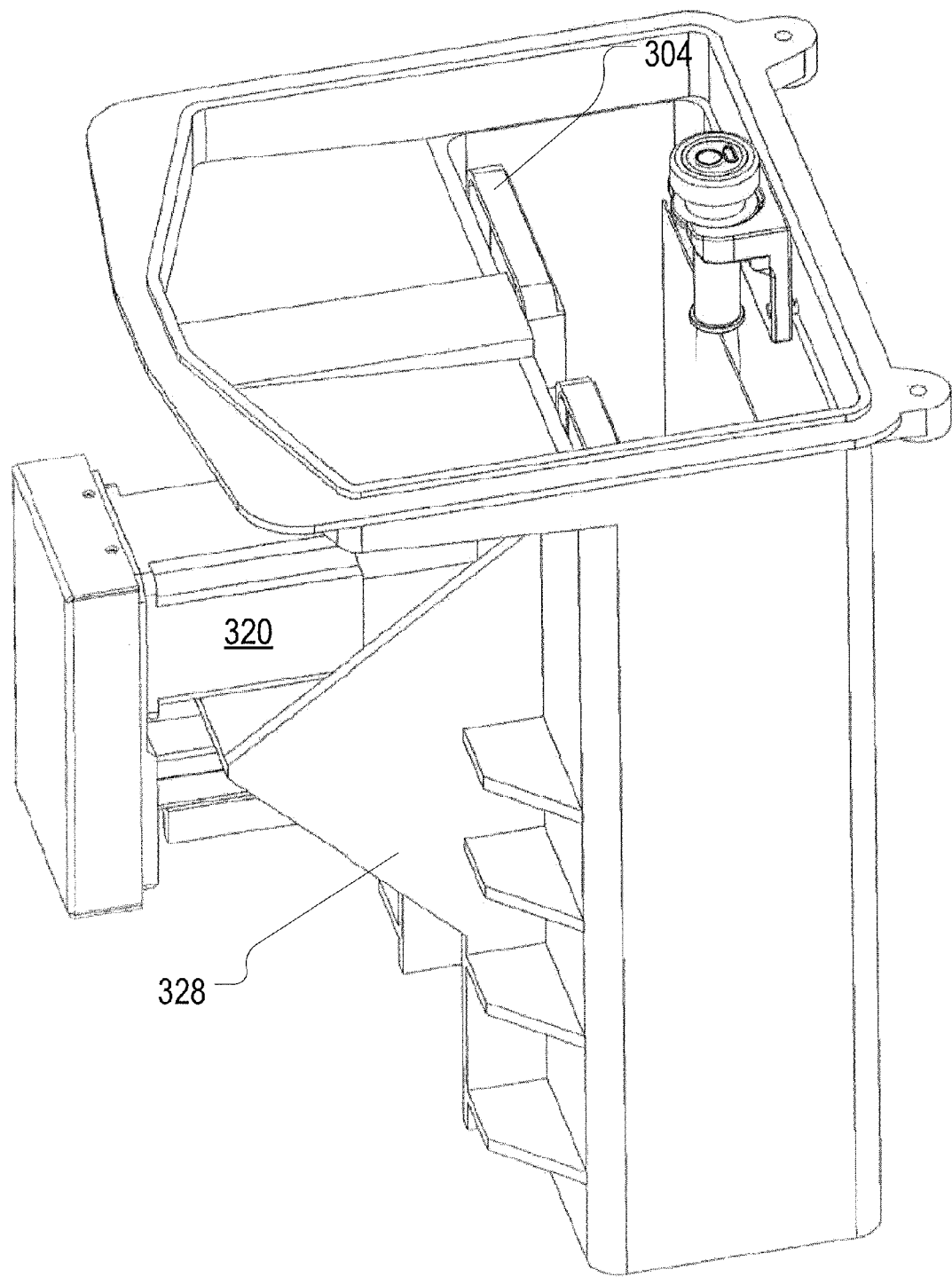
FIGS. 14A-B are views of yet another alternative arrangement of an irrigation mounting system.
Figure 14B:
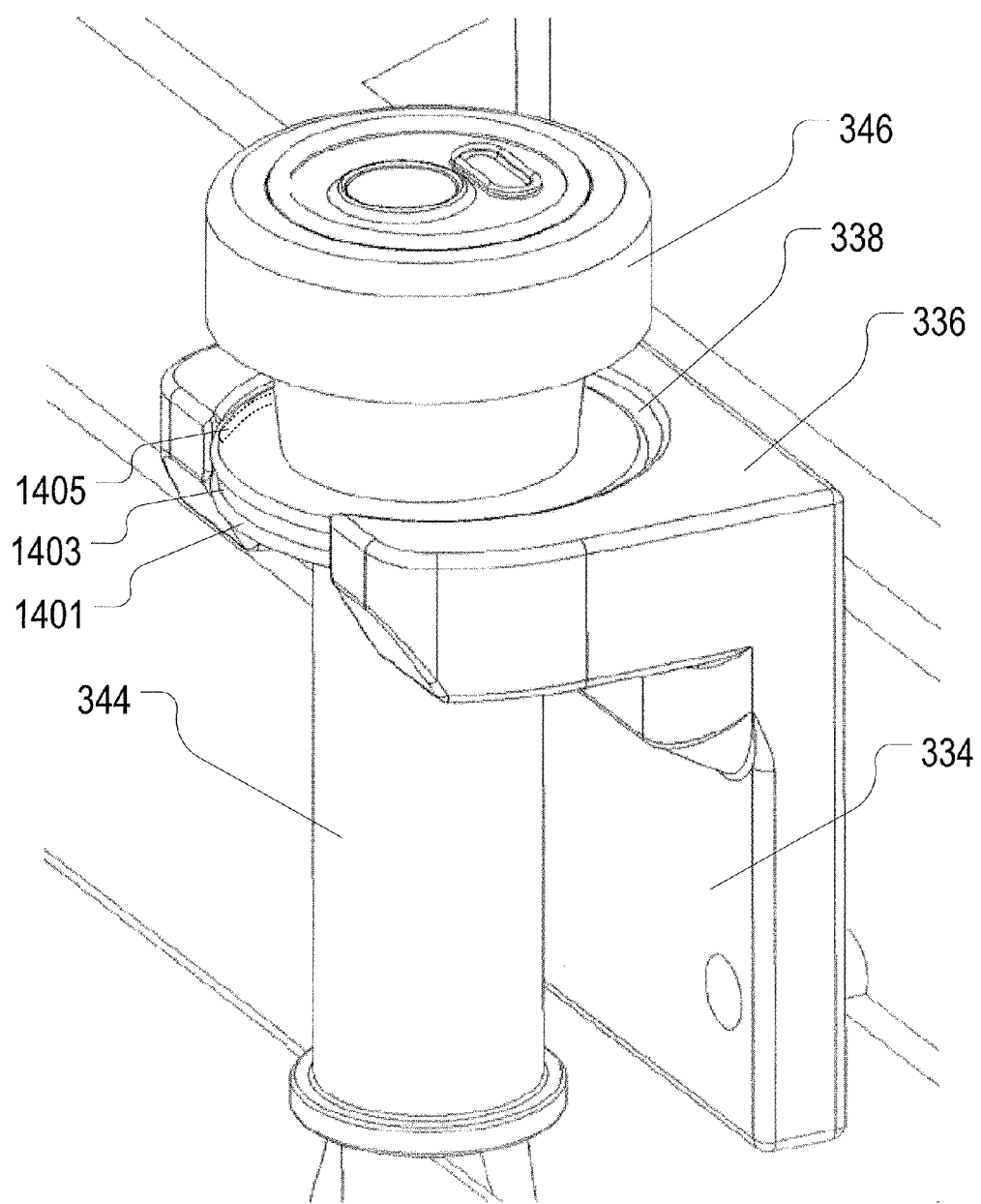

Irrigation container 310 is configured as a conventional irrigation container and includes a body portion 342 in which irrigation fluid is sealed, a neck member 344 extending from body portion 342, and a stopper member 346. Stopper member 346 includes an end portion 348 that is sized to be at least slightly larger than a diameter of opening 339 that leads into mounting aperture 338 formed on mounting platform 336. In one specific arrangement, end portion 348 is disc shaped having a diameter that is larger than the diameter of opening 339. However, it is understood that other shapes of end portion 348 may also be employed. For example, as seen in FIGS. 14A-B, the neck member 344 may include a washer-shaped portion 1401 configured to fit into mounting aperture 338. In some embodiments, the washer-shaped portion 1401 may have a larger diameter than the diameter of the mounting aperture 338 and, therefore, may sit inside the mounting aperture 338. In some embodiments, the washer-shaped portion 1401 may include a groove 1403 that mates with a raised portion 1405 on the inside of mounting aperture 338. Other shapes for the end portion 348 are also contemplated (e.g., tapered conical, elliptical, tear drop, etc).

To utilize irrigation mounting system 300, second plate 304 is moved away from first plate 302 so as to provide a gap between faces 312, 330 of first and second plates 302, 304, respectively. Once separated, irrigation container 310 is positioned between first and second plates 302, 304 such that neck member 344 is oriented to extend upwardly from body portion 342 of irrigation container 310. To retain irrigation container 310 within irrigation mounting assembly 300, a portion of stopper 346 is retained within mounting aperture 338 of mounting platform 336. More specifically, mounting aperture 338 is configured to receive a portion of stopper 346 below end portion 348. Because end portion 348 is slightly larger than mounting aperture 338, a bottom surface 350 engages a top surface 352 of mounting platform 336. In this manner, irrigation container 310 is thus suspended from mounting platform 336. Moreover, because mounting platform 336 extends laterally outwardly from first face 312 of first plate 302, irrigation container 310 permitted to freely suspend from mounting platform 336 such that it may articulate in response to changes in fluid levels within irrigation container 310.

Stopper 346 may be spiked and operatively connected to a fluid delivery system either before or after being secured to mounting platform 336. Once irrigation container 310 is secured to mounting platform 336, air entrained within irrigation container 310 will be disposed within a top portion of irrigation container 310, thus making the priming operation for the irrigation system effective to evacuate the air from irrigation container 310.

Once primed, motor 306 may be activated to move second plate 304 toward first plate 302, thereby compressing irrigation container 310 between first and second plates 302, 304 at a predetermined speed or time interval to effectively deliver irrigation fluid from irrigation container 310. In some embodiments, the speed of compression (e.g., the speed of the compression band 132 towards platen 126) may be constant throughout the delivery of the irrigation fluid 168. In some embodiments, the speed of compression may be variable. For example, the speed of compression may be based on a position of a footswitch or on compression speed versus time plot (e.g., provided by the surgeon or console). In some embodiments, the speed of compression may be adjusted to compensate for different fluid amounts in the irrigation container. For example, the compressing band 132 may need to be compressed at different rates (based, for example, on the irrigation container configuration and/or amount of remaining irrigation fluid 168) during an irrigation container's life cycle to provide the same flow of irrigation fluid 168. Other rates of compression are also contemplated by the present disclosure. Because irrigation container 310 is suspended from mounting platform 336, it may freely articulate in response to the changing shape of irrigation container 310 as it is compressed between first and second plates 302, 304.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. An irrigation mounting arrangement for an irrigation container defined by a body portion, a neck member, and a stopper, the irrigation mounting arrangement comprising:
   an upwardly extending base member; and
   a mounting arm mechanism extending away from the base member;
   wherein the mounting arm mechanism further comprises at least one mounting aperture configured to selectively receive a portion of the irrigation container such that the neck member of the irrigation container is oriented above the body portion during delivery of fluid from the irrigation container.

2. The irrigation mounting arrangement of claim 1, wherein the mounting arm mechanism is configured as a generally planar platform and the mounting aperture is formed therein.

3. The irrigation mounting arrangement of claim 2, further comprising an opening formed on an edge of the platform, the opening in communication with the mounting aperture.

4. The irrigation mounting arrangement of claim 3, wherein the opening is formed in an edge that is oriented so as to oppose the base member.

5. The irrigation mounting arrangement of claim 3, wherein the opening is formed in an edge that is oriented so as to be generally perpendicular to the base member.

6. The irrigation mounting arrangement of claim 2, further comprising a groove disposed around the mounting aperture.

7. The irrigation mounting arrangement of claim 1, wherein the mounting arm mechanism further comprises first and second laterally opposing mounting arms, each mounting arm including the mounting aperture formed therein.

8. The irrigation mounting arrangement of claim 7, wherein the first and second mounting arms are pivotally connected to the base member.

9. The irrigation mounting arrangement of claim 8, further comprising a biasing member connecting first and second mounting arms together.

10. The irrigation mounting arrangement of claim 1, further comprising a post member, wherein the post member is fixedly connected to the base member and the mounting arm mechanism is connected to the post member.

11. The irrigation mounting arrangement of claim 1, further comprising a clip member that is configured to attach to the neck member of the irrigation container, wherein the clip member engages the mounting aperture to suspend the irrigation container such that the neck member is disposed above the body portion of the irrigation container.

12. The irrigation mounting arrangement of claim 11, wherein the clip member has a contoured shape that includes a tapered conical, elliptical, or tear drop shape.

13. The irrigation mounting arrangement of claim 1, further comprising at least one plate member against which a portion of irrigation container is compressed.

14. The irrigation mounting arrangement of claim 13, wherein the plate member has a generally curved shape defining a mounting face.

15. The irrigation mounting arrangement of claim 14, further comprising a groove formed in the mounting face that is sized to receive the neck member.

16. The irrigation mounting arrangement of claim 14, further comprising a compressing band that is selectively moved toward the mounting face to compress the irrigation container between the compressing band and the mounting face.

17. The irrigation mounting arrangement of claim 16, wherein the compressing band is connected to a take-up reel that is operatively connected to a motor.

18. The irrigation mounting arrangement of claim 13, further comprising first and second plates, wherein the first plate is configured to be generally stationary and the second plate is configured to be selectively moved toward the first plate, wherein the mounting arm mechanism is oriented to suspend the irrigation container forward of a front face of the first plate.

19. The irrigation mounting arrangement of claim 18, wherein the second plate is connected to an actuation arm that is operatively connected to a motor.

20. The irrigation mounting arrangement of claim 1, wherein the irrigation container is mounted to the mounting arm mechanism such that the irrigation container may selectively articulate.

* * * * *